United States Patent [19]

Boesten et al.

[11] 4,080,259

[45] Mar. 21, 1978

[54] PROCESS OF PREPARING L AND D α-AMINO ACIDS BY ENZYME TREATMENT OF DL-α-AMINO ACID AMIDE

[75] Inventors: Wilhelmus Hubertus Joseph Boesten, Sittard; Lucia Redempta Maria Meyer-Hoffman, Munstergeleen, both of Netherlands

[73] Assignee: Novo Industri A/S, Denmark

[21] Appl. No.: 756,969

[22] Filed: Jan. 4, 1977

[30] Foreign Application Priority Data

Jan. 8, 1976   Luxembourg ............................ 74142

[51] Int. Cl.$^2$ ......................... C12D 13/06; C12B 1/00
[52] U.S. Cl. ........................................... 195/2; 195/29; 195/65
[58] Field of Search ...................... 195/2, 29, 65, 66 R

[56] References Cited

PUBLICATIONS

Hegeman, Journal of Bacteriology Mar. 1966, vol. 91, pp. 1140–1154.

Primary Examiner—Lionel M. Shapiro
Attorney, Agent, or Firm—Watson, Cole, Grindle & Watson

[57] ABSTRACT

A method of producing enzyme preparations having L-α-amino acyl amidase activity comprising cultivating a micro-organism selected from the group consisting of *Pseudomonas putida, Pseudomonas reptilivora,* and *Pseudomonas arvilla* in a nutrient medium and separating an enzyme preparation from said nutrient medium.

A process of preparing L-α-amino acid and D-α-amino acid amide from DL-α-amino acid amide by contacting said DL-α-amino acid amide with an enzyme preparation obtained by cultivating a micro-organism selected from the group consisting of *Pseudomonas putida, Pseudomonas reptilivora,* and *Pseudomonas arvilla* in the presence of a nutrient medium and separating the L-α-amino acid and D-α-amino acid amide thus formed.

6 Claims, No Drawings

PROCESS OF PREPARING L AND D α-AMINO ACIDS BY ENZYME TREATMENT OF DL-α-AMINO ACID AMIDE

BACKGROUND OF THE INVENTION

It is well known that some micro-organisms such as *Aspergillus oryzae, Aspergillus parasiticus, Mycobacterium phlei, Aeromonas proteolytica, Bacillus subtilis,* and *Bacillus stearothermophilus* can produce enzymes which are capable of hydrolyzing α-amino acid amides so as to form α-amino acid in an aqueous medium.

These prior art enzymes which in the following are referred to as α-amino acyl amidases show a highly stereo-specific activity and hydrolyze only L-α-amino acyl amides. Thus, D-α-amino acyl amides are substantially unaffected by these enzymes.

Therefore, these α-amino acyl amidases are suitable for effecting an optical resolution of DL-α-amino acids. In such a process, α-amino acyl amidase is contacted with DL-α-amino acid amide to effect a hydrolysis of the L-α-amino acid amide to form the corresponding amino acid, and the amino acid formed and/or the remaining D-α-amino acid amide is isolated [Greenstein & Winitz: "Chemistry of the amino-acids", vol. 3, pp. 1778–1781 (New York 1961)].

The object of the invention is to provide a preparation having an improved L-α-amino acyl amidase activity compared to the preparations obtained by the above-mentioned prior art method.

A further object of the invention is to provide a preparation having a high L-α-amino acyl amidase activity and without undesired enzymatic side effects.

A still further object of the invention is to provide a process of preparing L-α-amino acid and/or D-α-amino acid amide from DL-α-amino acid amide.

SUMMARY OF THE INVENTION

The method of the invention comprises cultivating a micro-organism selected from the group consisting of *Pseudomonas putida, Pseudomonas reptilivora,* and *Pseudomonas arvilla* in the presence of a nutrient medium containing assimilable sources of carbon, nitrogen and phosphorus.

By cultivating these micro-organisms in a manner which is well known per se, preparations are obtained having an exceptionally high amidase activity.

The micro-organisms used in the method of the invention are described in Bergey's Manual of determinative bacteriology (Baltimore 1975).

Preferred strains are *Pseudomonas putida* ATCC 12633, ATCC 25571, ATCC 17390, ATCC 17426 and ATCC 17484, *Pseudomonas reptilivora* ATCC 14039, and *Pseudomonas arvilla* ATCC 23974.

These strains are available from American Type Culture Collection, Washington DC, U.S.A.

*Pseudomonas putida,* and, in particular, the strain ATCC 12633 is a particularly preferred micro-organism.

*Pseudomonas putida* is described in the literature as capable of producing mandelic acid racemase.

It is, therefore, surprising that *Pseudomonas putida* produces an enzyme having a stereo-specific amidase activity, and does not cause racemization of e.g. phenylglycine which is closely related to mandelic acid.

The micro-organisms used in the method of the invention can be cultivated in ordinary nutrient media, e.g. as described by Hegeman in Journal of Bacteriology, 91, page 1140 (1966).

The micro-organisms are preferably cultivated at a temperature within the range of from 30° to 35° C under aerobic conditions.

In most cases, the addition of growth factors or inductors is unnecessary. The addition of yeast extract appears to have a favourable influence on the production of the enzyme. After an incubation period of between about 2 and about 30 hours, the cells may be harvested, preferably during the period of exponential growth.

A preparation having α-amino acyl amidase activity may be obtained by precipitating the cells, optionally by using a flocculating agent. The cells may also be cross-linked or bonded to or absorbed on a carrier. In some cases, it may be desirable to modify the cell walls, e.g. by a heat treatment, to render the enzyme more accessible. A crude preparation may also be obtained by destroying the cells and recovering the enzyme by extraction, filtration and optionally spray-drying.

A preparation consisting of pure enzyme may be recovered in a conventional manner from the crude product described above. Pure enzyme or enzyme preparations may also be obtained from the culture medium by well known techniques.

The invention also relates to a process of preparing L-α-amino acid and D-α-amino acid amide from DL-α-amino acid amide by contacting said DL-α-amino acid amide with a preparation having L-α-amino acyl amidase activity.

This process is characterized in using a preparation obtained by cultivation of a micro-organism selected from the group consisting of *Pseudomonas putida, Pseudomonas reptilivora,* and *Pseudomonas arvilla* in the presence of a nutrient medium containing assimilable sources of carbon, nitrogen, and phosphorus.

The preparation having L-α-amino acyl amidase activity is preferably contacted with the DL-α-amino acid amide in an aqueous medium at a temperature of between 0° and 60° C, and most preferred at a temperature of between 20° and 40° C, and at a pH value of between 6 and 10.5, and more preferred of between 7.5 and 9.5.

Outside these ranges, the activity and/or the stability of the enzyme is generally insufficient for practical use. The enzyme may be activated in a well known manner, e.g. by the addition of a metal compound such as a magnesium, manganese, or zinc compound.

The weight ratio of the (unpurified) enzyme to the substrate may vary within wide ranges, e.g. between 1:25 and 1:750. If a pure enzyme is used, a higher ratio may be utilized.

When the hydrolysis of the L-α-amino acid amide has been completed, the free acid may be separated from the remaining D-α-amino acid amide, and the latter compound may then be hydrolized so as to form D-α-amino acid.

The process of the invention is suitable for isolating optically active natural or synthetic α-amino acids such as the D- and/or L-form of phenylalanine, 3,4-dihydroxyphenylalanine, tyrosine, methionine, leucine, alanine, phenylglycine, 4-hydroxyphenylglycine, 4-alkoxyphenylglycine and other substituted phenylglycines.

The invention will now be described in further detail with reference to the following examples.

EXAMPLE I

*Pseudomonas putida* ATCC 12633 was incubated at 28° – 30° C in a flask placed on a rotating shaker. The growth was measured with a spectrophotometer at λ=680 nm. A nutrient medium of pH 6.85 was prepared by mixing: 1 liter of distilled water, 8.95 g secondary sodium phosphate dodecahydrate, 3.4 g primary potassium phosphate, 1.0 g ammonium sulphate, 200 mg nitrilotriacetic acid, 580 mg magnesium sulphate heptahydrate, 67 mg calcium chloride dihydrate, 2.0 mg ferrous sulphate heptahydrate, 0.2 mg ammonium paramolybdate, and 1 ml "Hutner's metals 44" [a diluted solution of zinc, iron, manganese and copper sulphate, cobalt nitrate, sodium perborax, and E.D.T.A. — described in J. Cellular & Compar. Physiol. 49, pp. 25–68 (1957)]. The mixture was then sterilized and subsequently cooled, and finally 2 g asparagine and 2 g DL-mandelic acid were added.

The cells were harvested during the exponential growth phase by centrifugation (30 minutes at 10,000 rpm with cooling). The solid thus obtained was washed with 0.1 molar phosphate buffer at a pH of 6.8 and once again centrifuged (20 minutes at 10,000 rpm). The solid was suspended in the phosphate buffer (40 g wet cells in 100 ml buffer), whereafter the cell walls were destroyed with an ultrasonic cell desintegrator (20 kc/s for 20 minutes at 0° C). A crude extract was obtained by removing the solid particles by centrifugation (30 minutes, 10,000 rpm at 4° C). The yield of cell extract, calculated as dry substance, amounted to 0.8 g per liter of culture liquid.

EXAMPLE II

The procedure of Example I was repeated, except that a medium containing 10 g of yeast extract (added before the sterilization) was used instead of asparagine. The yield of cell extract amounted to approximately 1.2 g of dry substance per liter of culture liquid.

EXAMPLE III

The procedure of Example I was repeated, except that a culture medium containing 10 g of yeast extract was used instead of asparagine and mandelic acid. The yield of cell extract amounted to 1.25 g of dry substance per liter of culture liquid.

EXAMPLE IV

In a flask provided with a stirrer, 1.5 ml of 0.125 molar $MgCl_2$, ½ ml of 0.025 molar $MnCl_2$, and 0.1 ml crude cell extract (dry weight 7 mg) prepared as described in Example III were added to a solution of 2.0 g (13.3 mgmoles) of L-phenylglycineamide in 48 ml of water, with stirring, at 25° C. During the reaction the pH of the reaction mixture rose from 9.6 to 9.7.

After 20 hours, the reaction mixture was acidulated with 4N hydrochloric acid to a pH of 6.5. L-phenylglycine which then crystallized out was removed by filtration on a glass filter and washed on the filter with 2 portions of 10 ml of water and subsequently with 2 portions of 10 ml of acetone. After drying, 1.6 g of L-phenylglycine (yield: 80%) were obtained.

The specific rotation of the L-phenylglycine was: $[\alpha]_D^{20} = 157.7°$ (C = 1.6; 2.6% by weight of HCl). From literature is known (see Beilstein 14 III, page 1188) that $[\alpha]_D^{20} = 157.5°$ (C = 1.6; 2.6% by weight of HCl).

EXAMPLE V

In a flask provided with a stirrer, 4.0 g (26.6 mgmoles) of DL-phenylglycineamide, 3 ml of 0.125 molar $MgCl_2$, 1 ml of 0.025 molar $MnCl_2$ and 1 ml of crude cell extract (dry weight 70 mg) prepared as described in Example III were added to 97 ml of water. This mixture was subsequently stirred for 20 hours at 25° C.

After said reaction time, the L-phenylglycine formed was removed by filtration, and the filtrate passed over 75 ml of Dowex 21 K exchanger on the $OH^-$ form. Next, the exchanger was washed with 150 ml of water and the combined eluates concentrated by evaporation (40° C; 12 mm Hg). 1.8 g of D-phenylglycineamide (yield: 90%) were obtained. This product was pure according to thin-layer chromatography.

In order to determine the optical purity and for a comparison with the literature, the amide was converted into the corresponding hydrochloric acid salt. To this end, 1.0 g of D-phenylglycineamide was dissolved in 20 ml of methanol, followed by filtration and addition of 1.5 ml of concentrated hydrochloric acid to the filtrate. 20 ml of acetone were then added, the D-phenylglycineamide, HCl formed then filtered on a glass filter and washed on the filter with 2 portions of 20 ml of acetone. 0.9 g of D-phenylglycineamide, HCl was obtained.

The specific rotation was:
$[\alpha]_D^{20} = -101.2°$ (C = 0.8; water).

It appears from the literature (Beilstein 14 III, page 1189) that $[\alpha]_D^{20} = -100.8°$ (C = 0.8; water).

EXAMPLE VI

In this example the rates of hydrolysis of L-phenylglycineamide and L-leucine amide are compared after 36 and 60 minutes when using an enzyme preparation obtained from *Pseudomonas putida*.

To a solution of 150.0 mg (1.0 mgmole) of L-phenylglycineamide in 15 ml of water, 0.5 mg of $MnCl_2$ and 2 mg of $MgCl_2$ and, subsequently, 0.10 ml of crude cell extract (7 mg dry weight) prepared as described in Example III were added. Following make-up with water to 25.0 ml samples were taken after 36 and 60 minutes, and the number of mgmoles of L-phenylglycine contained in each sample was determined by amino acid analysis.

In the same way and with a similar amount of cell extract, 130.0 mg (1 mgmole) of leucine amide were converted. Here, again, samples were taken after 36 and 60 minutes.

| Results: | 36 minutes | 60 minutes |
|---|---|---|
| L-phenylglycineamide | 0.63 mgmole/25 ml | 0.88 mgmole/25 ml |
| L-leucineamide | 0.16 mgmole/25 ml | 0.28 mgmole/25 ml |

EXAMPLE VII 1.0 mgmole of each of the following α-amino acid amides was converted at 20° C with 0.1 ml of crude cell extract (dry weight 7 mg), prepared as described in Example III, in 5 ml of water in which 0.5 mg of $MnCl_2$ and 2.0 mg of $MgCl_2$ had been dissolved. After 3 and 18 hours, an amino acid analysis was conducted.

| | % by weight of amino acid | |
|---|---|---|
| | after 3 hours | after 18 hours |
| L-phenylglycineamide | 98 % | 99 % |
| L-methioineamide | 97 % | 99 % |
| L-p-hydroxyphenylglycineamide | 92 % | 98 % |
| L-leucineamide | 57 % | 98 % |
| DL-α-amino-δ-cyanovaleramide | 42 % | 51 % |
| L-phenylalanineamide | 34 % | 96 % |
| L-tyrosineamide | 29 % | 96 % |
| Glycineamide | 1 % | 3 % |
| DL-α-aminocaprolactam | 0 % | 0 % |

EXAMPLE VIII

Substrate solutions each having the following composition were prepared: 5 ml water, 100 mg L-phenylglycineamide, 0.5 mg $MnCl_2$ and 2 mg $MgCl_2$.

Substrates of said composition were treated with 0.1 ml of crude cell extract (dry weight 2 mg) of each of the micro-organisms set forth in the following table. After ½ and 1½ hours, an amino acid analysis was carried out.

| | % by weight of amino acid | |
|---|---|---|
| | after ½ hour | after 1½ hours |
| Aspergillus oryzae | 0 % | 1 % |
| Aspergillus parasiticus | 0 % | 1 % |
| Bacillus subtilis | 1 % | 2 % |
| Pseudomonas putida | 34 % | 72 % |
| Bacillus stearothermophilus | 2 % | 3 % |
| Aeromonas proteolitica | 21 % | 48 % |

As will appear from the above table, the enzyme preparation obtained by the cultivation of *Pseudomonas putida* has a significantly higher activity than the enzyme preparations obtained by the cultivation of the remaining micro-organisms.

EXAMPLE IX

Enzyme preparations were prepared as described in Example III, using the micro-organisms *Pseudomonas reptilivora* ATCC 14039 and *Pseudomonas arvilla* ATCC 23974. The yields of crude cell extract, expressed as grams per liter of culture liquid, were 1.24 g/l and 0.82 g/l, respectively.

The α-amino acyl amidase activity using L-phenylglycine-amide as substrate was tested using 0.1 ml of cell extract (dry weight 4 mg) and a solution consisting of 0.2 g L-phenylglycineamide, 0.3 ml of 0.25 molar $MnCl_2$, 1.2 ml of 0.125 molar $MgCl_2$ and 23.5 ml water.

After one hour, an amino acid analysis showed that the conversion to L-phenylglycine was 46.8% for the preparation from *Pseudomonas reptilivora* and 35.7% for that from *Pseudomonas arvilla*.

The example was repeated, except that the enzyme preparations were obtained by using *Pseudomonas aeruginosa, Pseudomonas fluorescens* and *Pseudomonas stutzeri*, respectively. After one hour, the conversion to L-phenylglycine was 21.4%, 9.6%, and 4.2%, respectively.

EXAMPLE X

The selective hydrolysis to form L-4-hydroxyphenylglycine was determined by dissolving 0.071 g (0.43 millimoles) DL-4-hydroxyphenylglycineamide in 24 ml water and adding to this solution 25.1 mg of an enzyme preparation obtained by spray-drying the culture liquid from a culture of *Pseudomonas putida*. The pH of the mixture was 8.2. The mixture was maintained at 30° C with stirring for 3 hours. Every thirty minute, a 2 ml sample was taken. The sample was diluted with 2 ml of 0.333 N sulfuric acid, and the content of L-4-hydroxyphenylglycine was determined by amino acid analysis. From these data, the amount of the L-amino acid amide which had been hydrolysed could be calculated. The results are summarized below. No hydrolysis of the D-amino acid amide occurred.

| time (hours) | mole % of L-4-hydroxyphenylglycineamide hydrolysed |
|---|---|
| 0.5 | 65 |
| 1 | 88 |
| 1.5 | 93 |
| 2 | 99 |
| 2.5 | 99 |
| 3 | 99 |

EXAMPLE XI

The hydrolysis of DL-4-methoxyphenylglycineamide was determined as described in Example X, using 1.36 g DL-4-methoxyphenylglycineamide, 43 ml water and 49.3 mg of the enzyme preparation obtained by spray-drying a *Pseudomonas putida* culture liquid.

Sampling and determination of the L-amino acid were also carried out as described above.

No hydrolysis of the D-amino acid amide occurred.

| time (hours) | mole % of L-4-methoxyphenylglycineamide hydrolysed |
|---|---|
| 0.5 | 18 |
| 1.0 | 41 |
| 1.5 | 61 |
| 2.0 | 77 |
| 2.5 | 91 |
| 3 | 99 |

We claim:

1. A process for preparing L-α-amino acid and D-α-amino acid amide from DL-α-amino acid amide by contacting said DL-α-amino acid amide with a preparation having α-amino acyl amidase activity, said enzyme preparation being obtained by cultivating a micro-organism selected from the group consisting of *Pseudomonas putida, Pseudomonas reptilivora*, and *Pseudomonas arvilla* in the presence of a nutrient medium containing assimilable sources of carbon, nitrogen, and phosphorus.

2. A method as in claim 1 for the preparation of L-phenylglycine and D-phenylglycineamide from DL-phenylglycineamide, in which the preparation used is obtained from a culture of *Pseudomonas putida*.

3. A method as set forth in claim 1, in which the enzyme preparation is obtained by cultivating a *Pseudomas putida* micro-organism in the presence of said nutrient medium.

4. A method as set forth in claim 1, in which the enzyme preparation is obtined by cultivating a *Pseudomas reptilivora* micro-organism in the presence of said nutrient medium.

5. A method as set forth in claim 1, in which the enzyme preparation is obtained by cultivating a *Pseudomas arvilla* micro-organism in the presence of said nutrient medium.

6. A method as set forth in claim 1, in which the enzyme preparation is obtained by cultivating *Pseudomas putida* ATCC 12633, or a mutant thereof in the presence of said nutrient medium.

* * * * *